US006694180B1

(12) United States Patent
Boesen

(10) Patent No.: US 6,694,180 B1
(45) Date of Patent: *Feb. 17, 2004

(54) WIRELESS BIOPOTENTIAL SENSING DEVICE AND METHOD WITH CAPABILITY OF SHORT-RANGE RADIO FREQUENCY TRANSMISSION AND RECEPTION

(76) Inventor: Peter V. Boesen, 4026 Beaver Ave., Des Moines, IA (US) 50310

( * ) Notice: Subject to any disclaimer, the term of this patent is extended or adjusted under 35 U.S.C. 154(b) by 0 days.
This patent is subject to a terminal disclaimer.

(21) Appl. No.: 09/750,951

(22) Filed: Dec. 28, 2000

Related U.S. Application Data

(63) Continuation-in-part of application No. 09/640,230, filed on Aug. 16, 2000, and a continuation-in-part of application No. 09/619,233, filed on Jul. 19, 2000, and a continuation-in-part of application No. 09/607,305, filed on Jun. 30, 2000, and a continuation-in-part of application No. 09/587,743, filed on Jun. 5, 2000, now Pat. No. 6,408,081, and a continuation-in-part of application No. 09/570,758, filed on May 15, 2000, now Pat. No. 6,470,893, and a continuation-in-part of application No. 09/560,205, filed on Apr. 28, 2000, and a continuation-in-part of application No. 09/416,168, filed on Oct. 11, 1999.

(51) Int. Cl.[7] ................................................ A61B 5/05
(52) U.S. Cl. ...................................................... 600/547
(58) Field of Search ................................. 600/300, 484, 600/485; 128/903, 904; 119/174; 381/312; 604/97.03

(56) References Cited

U.S. PATENT DOCUMENTS

| 4,150,262 | A | 4/1979 | Ono |
| 4,248,241 | A | 2/1981 | Tacchi |
| 4,334,315 | A | 6/1982 | Ono et al. |
| 4,374,382 | A | 2/1983 | Markowitz |
| 4,528,987 | A | 7/1985 | Slocum |

(List continued on next page.)

FOREIGN PATENT DOCUMENTS

| EP | 0 683 621 A | 11/1995 |
| GB | 2 074 817 | 11/1981 |
| WO | WO 98/34530 | 8/1998 |

OTHER PUBLICATIONS

Article entitiled Agilent Technologies Announces Availability of Wireless Network Cap for Portable Patient Monitor, http://www.healthcare.agilent.com/press_releases/PRHS2920030.html.
Article entitled "Agilent Technologies Introduces New Telemon Patient Monitor," http://www.healthcare.agilent.com/press releases/PRHS2920016.html.
Article entitled "M3 and M4 Series Patient Monitors," http://www.healthcare.agilent.com/show_product.pl?M3%20and%20M4%20Series%20Patient%20Monitor.html.
Article entitled "What is a Wireless LAN?", 1998, Proxim, Inc.
Bluetooth Usage Model, http://www.bluetooth.com/bluetoothguide/models/ultimate.asp (visited Jun. 26, 2000).

(List continued on next page.)

Primary Examiner—Eric F. Winakur
Assistant Examiner—Nikita R Veniaminov
(74) Attorney, Agent, or Firm—McKee, Vorhees & Sease, P.L.C.

(57) ABSTRACT

Devices, systems and methods related to biopotential sensing and medical monitoring are disclosed. Biopotential sensor units include a transmitter for wirelessly transmitted the biopotential information. The transmitter may be limited by its transmission power and range in order to reduce electromagnetic interference. The biopotential sensors include an external auditory canal temperature sensor, an ear pulse oximeter, and a hypnotic state sensing EEG. The sensor units communicate with a patient monitor unit located on a patient. The patient monitor unit wirelessly communicates with a central station.

17 Claims, 8 Drawing Sheets

U.S. PATENT DOCUMENTS

| | | |
|---|---|---|
| 4,588,867 A | 5/1986 | Konomi |
| 4,635,646 A | 1/1987 | Gilles et al. |
| 4,654,883 A | 3/1987 | Iwata |
| 4,672,976 A | 6/1987 | Kroll |
| 4,723,555 A | 2/1988 | Shue |
| 4,742,831 A | 5/1988 | Silvian |
| 4,770,189 A | 9/1988 | Shyu |
| 4,773,427 A | 9/1988 | Inoue et al. |
| 4,777,961 A | 10/1988 | Saltzman |
| 4,791,673 A | 12/1988 | Schreiber |
| 4,791,933 A | 12/1988 | Asai et al. |
| 4,792,145 A | 12/1988 | Eisenberg et al. |
| 4,854,328 A * | 8/1989 | Pollack .................. 119/174 |
| 4,865,044 A * | 9/1989 | Wallace et al. ............ 128/903 |
| 4,947,859 A | 8/1990 | Brewer et al. |
| 4,981,139 A * | 1/1991 | Pfohl .................. 600/484 |
| 5,010,890 A | 4/1991 | Pfohl et al. |
| 5,035,247 A | 7/1991 | Heimann |
| 5,052,398 A | 10/1991 | Gober |
| 5,191,602 A | 3/1993 | Regen et al. |
| 5,201,007 A | 4/1993 | Ward et al. |
| 5,280,524 A | 1/1994 | Norris |
| 5,295,193 A | 3/1994 | Ono |
| 5,298,692 A | 3/1994 | Ikeda et al. |
| 5,343,532 A | 8/1994 | Shugart, III |
| 5,365,937 A | 11/1994 | Reeves et al. |
| 5,381,798 A | 1/1995 | Burrows |
| 5,387,194 A * | 2/1995 | Williams et al. ......... 604/97.03 |
| 5,417,222 A | 5/1995 | Dempsey et al. |
| 5,422,934 A | 6/1995 | Massa |
| 5,458,123 A | 10/1995 | Unger |
| 5,464,017 A * | 11/1995 | Juang .................. 600/485 |
| 5,492,129 A | 2/1996 | Greenberger |
| 5,613,222 A | 3/1997 | Guenther |
| 5,634,468 A | 6/1997 | Platt et al. |
| 5,692,059 A | 11/1997 | Kruger |
| 5,704,351 A * | 1/1998 | Mortara et al. ............ 128/904 |
| 5,721,783 A | 2/1998 | Anderson |
| 5,771,438 A | 6/1998 | Palermo et al. |
| 5,933,506 A | 8/1999 | Aoki et al. |
| 5,987,146 A | 11/1999 | Pluvinage et al. |
| 6,021,207 A | 2/2000 | Puthuff et al. |
| 6,112,103 A | 8/2000 | Puthuff |
| 6,113,539 A * | 9/2000 | Ridenour .................. 600/300 |
| 6,181,801 B1 | 1/2001 | Puthuff et al. |
| 6,402,689 B1 * | 6/2002 | Scarantino et al. ......... 128/903 |
| 6,408,081 B1 * | 6/2002 | Boesen ................. 381/312 |
| 6,470,893 B1 * | 10/2002 | Boesen ................. 128/899 |

OTHER PUBLICATIONS

Article entitled "Wireless Worries: Are Cell Phones a Danger to You and Your Children," May 26, 2000, http://more.abcnews.go.com/onair/2020/2020_000526_cellphones.html.

Air Magic Wireless Headset User Guide.

Article entitled "A One–Size Disposable Hearing Aid Is Introduced," by Wayne J. Staab, Walter Sjursen, David Preves & Tom Squeglia, pp. 36–41, The Hearing Journal, Apr. 2000, vol. 53, No. 4.

Article entitled "Brain cancer victim sues cell–phone providers," http://www.cnn.com/2000/TECH/computing/08/08/cellular.cancer.lawsuit.idg/index.html.

Article entitled "Report Urges Curbs on Mobile Phone Use," May 15,2000, http://www.techweb.com/wire/story/TWB20000515S005.

Article entitled "Scientist link eye cancer to mobile phones," by Jonathan Leake, Jan. 14, 2001, http://www.Sunday-times.co.uk/news/pages/sti/2001/01/14/stinwenws01032.html.

Article entitled "The Hearing Review," Jan. 1999, vol. 3: Hearing in Noise (Supplement) pp. 1–62.

Article entitled "The latest on cell phone emissions".

Article entitled "U.S. Will Oversee Cell–Phone Safety Studies," Jun. 9, 2000, http://www.techweb.com/wire/story/reutrers/REU20000609S0003.

Article entitled, "A new level of Control for Faster, More Predictable Recovery," by Medical Aspect, as early as 1997.

* cited by examiner

WIRELESS BIOPOTENTIAL SENSING DEVICE AND METHOD WITH CAPABILITY OF SHORT-RANGE RADIO FREQUENCY TRANSMISSION AND RECEPTION

RELATED APPLICATIONS

This application is a continuation-in part to related applications: U.S. application Ser. No. 09/587,743 filed Jun. 5, 2000 now is a U.S. Pat. No. 6,408,081; U.S. application Ser. No. 09/607,305 filed on Jun. 30, 2000; U.S. application Ser. No. 09/570,758 filed on May 15, 2000 now is a U.S. Pat. No. 6,430,893; U.S. application Ser. No. 09/560,205 filed on Apr. 28, 2000; U.S. application Ser. No. 09/640,230 filed on Aug. 16, 2000; U.S. application Ser. No. 09/619,233 filed on Jul. 19, 2000; U.S. application Ser. No. 09/416,168 filed on Oct. 11, 1999; the U.S. Application entitled APPARATUS, METHOD AND SYSTEM FOR ULTRA SHORT RANGE COMMUNICATION by Peter V. Boesen, M.D., filed on Nov. 7, 2000.

BACKGROUND OF THE INVENTION

1. Field of the Invention

The present invention relates to devices and methods for monitoring biopotentials. More particularly, but without limitation, the present invention relates to a method and device for monitoring or sensing a biopotential and wirelessly transmitting the monitored condition.

2. Problems in the Art

Biopotential sensors are known in the art. In a conventional arrangement, such as with electrocardiograph (ECG) leads, the sensors/leads are connected to a bedside monitor through wires. The bedside monitor may also be wired to a nursing station or other central station for monitoring purposes. Thus there are two locations at which a patient's physiological condition needs to be monitored: (1) at the location of the patient and (2) at a nursing station or central station.

The use of wires to make these connections may create problems. For example, at times a patient connected to an ECG or other sensors may need to be moved very quickly to a different part of a hospital. In this scenario, the electrodes must either be removed from the patient or the monitor must be moved with the patient. Removing the electrodes or other sensors from the patient requires additional time. Later reconnecting the electrodes or sensors requires additional time as well. Other problems are introduced by the detachment of the electrodes as well, including additional patient discomfort as well as damage to the electrodes or weakening of the electrode interface. Thus there is a need in the art for a biopotential sensing device and method which minimizes the use of wire connections between a patient and a central station.

In some prior art devices, a portable monitoring device may be used that wirelessly transmits physiological information to a nursing station or central station. This eliminates some of the problems associated with wiring, in that the portable monitor may remain wired to a patient. However, problems remain, in that the wires between the patient's sensors and the portable monitoring device may still need to be detached in order to provide medical care to the patient. Thus there is a need for a medical monitoring system that minimizes the connections between a patient and a monitoring device.

Another prior art approach has involved the use of a sensor coupled with a transmitter, in order to remove the need for wires between the sensor and monitoring equipment. One example of this type of device is disclosed in U.S. Pat. No. 5,634,468, entitled Sensor Patch and System for Physiological Monitoring, issuing on Jun. 3, 1997. The prior art device provides for wireless transmission from a sensor to a receiver located on a patient and for communication via a standard telephone network from the receiver. Thus the problem of eliminating wires between a patient unit and a central monitoring station remain and other problems are introduced that are consistent with other problems of using wireless systems within a hospital environment.

One of these problems involves electromagnetic radiation. The medical and scientific community are beginning to realize the harmful effects that exposure to electromagnetic radiation can have on the human body and its vital organs. Any placement of a transmitter on the human body creates concerns regarding electromagnetic radiation exposure. This is particularly true with medical monitoring systems due to the proximity of the transmitter and the continuous operation of the device.

Another problem is electromagnetic interference. Electromagnetic interference affects the integrity of wireless systems, a problem which is acutely troublesome in critical care applications where if a system fails or otherwise improperly functions, a person may not receive medical care when needed. Increasing the number of wireless devices adds to the problem instead of addressing it or eliminating it. In a hospital setting, various other problems serve to compound the problem. One such problem is the current limitations on the amount of allocated frequency space for medical applications. Although spectral resources have been allocated for wireless telemetry medical services, this allocation is limited. Other available frequencies may share with other users, making these frequencies less suitable for critical care applications.

This limited availability of allocated frequencies further increases the likelihood that interference may occur within a hospital. Prior solutions have attempted to avoid the problem by making equipment operate at multiple frequencies. For example, in U.S. Pat. No. 5,458,123, entitled System for Monitoring Patient Location and Data, issuing on Oct. 17, 1995, a different carrier frequency is allocated to each patient.

Having equipment operate at user-selectable frequencies is simply a poor solution in critical care applications. This type of methodology is only useful where a particular electromagnetic interference problem has already been identified. For example, if two wireless patient monitors are operating in the same room, then it should be known that they should not be operating at the same frequency or else interference may result. Unfortunately, one does not always know when different frequencies should be selected, as electromagnetic interference is not generally so predictable. In some facilities the number of frequencies available may be smaller than the number of patients that need to be monitored, thus that two or more patients may be operating on the same frequency. Furthermore, manufacturing a device that can operate on so many different frequencies can dramatically increase the cost and size of the device. In addition, although operation on the same frequency may ensure interference, selection of different frequencies does not eliminate the possibility of electromagnetic interference.

Spread spectrum communications is another solution to electromagnetic interference that has been used in medical devices as well as various other industries. For example, in U.S. Pat. No. 5,381,798, entitled Spread Spectrum Telemetry of Physiological Signals, issuing on Jan. 17, 1995, a spread spectrum transmitter and a spread spectrum receiver are used to transmit ECG information. In spread spectrum communications, bandwidth is sacrificed in order to increase signal-to-noise ratios. An increased signal-to-noise ratio makes a device less susceptible to noise-type interference. Thus spread spectrum systems do have certain advantages, however, as more and more devices are used on the same frequencies, these advantages continue to decrease and there is a further need for bandwidth. Furthermore, increased transmission power may be required because the transmission is over a wider band. The increased transmission power is related to increased likelihood of interference and shortens battery life in a battery-operated transmitter. Thus many deficiencies in the prior art remain.

SUMMARY OF THE INVENTION

The present invention includes a new wireless biopotential monitoring system which has the advantages of limiting electromagnetic interference. The biopotential monitoring system includes a sensor unit having a transmitter. The sensor unit may include an external auditory canal temperature sensor according to the present invention, an earpiece pulse oximeter according to the present invention, or an ECG or other sensor. The biopotential monitoring system may also include a patient monitor for monitoring biopotentials and physiological conditions at or near the patient. The monitoring system may also include a monitor located at nursing station or central location. The transmitter in the sensor unit is adapted for low power transmissions.

The present invention also includes a method of medical monitoring that permits biosensors to sense physiological data and wirelessly transmit the physiological information from a plurality of sensors to a patient unit. The patient unit then interleaves the physiological information at the patient unit and wirelessly transmits the interleaved information to a monitor unit.

BRIEF DESCRIPTION OF THE DRAWINGS

The present invention is illustrated by way of example and not limitation in the figures of the accompanying drawings, in which like references indicate similar elements and in which.

DETAILED DESCRIPTION OF A PREFERRED EMBODIMENT

The present invention will be described as it applies to its preferred embodiment. It is not intended that the present invention be limited to the described embodiment. It is intended that the invention cover all modifications and alternatives which may be included within the spirit and scope of the invention.

Figure 1:
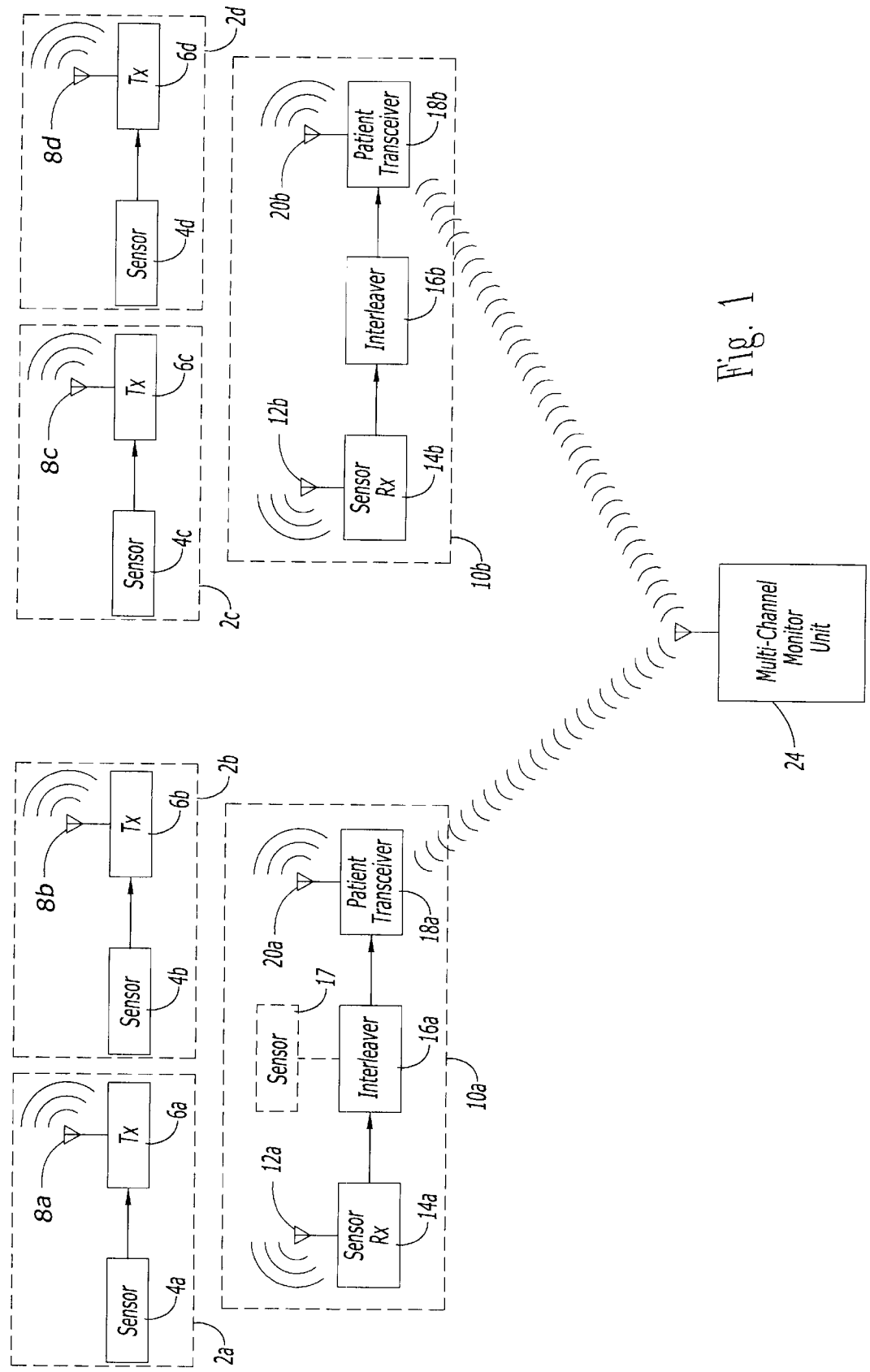
FIG. 1 is a block diagram of an embodiment of a medical monitoring system according to the present invention.

FIG. 1 shows a block diagram of a medical monitoring system and method according to an embodiment of the present invention. FIG. 1 depicts a number of sensor units 2a, 2b, 2c, and 2d. Each sensor unit 2 includes a sensor 4 and a transmitter 6 having an antenna 8. The antenna 8 may be internally located in the sensor unit 2. The sensor 4 may be a temperature sensor, a pulse oximeter, an electrocardiograph (ECG) or other medical or physiological condition monitoring sensor. The sensor senses a physiological conditions in order to provide physiological information. This information is sent from the sensor 4 to the transmitter 6 in the sensor unit. The transmitter 6 is a low-power transmitter that transmits an ultra-short range, such as less than approximately 12 feet. This transmitted signal is received by a patient unit 10 that is located on the patient and within the range of the transmitter 6. The patient unit 10 may receive information from multiple sensor units 2. When receiving information from multiple sensor units, the information may be encoded such as is well known in electronic communications or as may be performed by off-the-shelf transmitters or integrated circuits used in the transmitter. Where a digital communications channel is used, an identifier associated with each sensor unit can be used to identify the source of the information. It is to be appreciated, that due to the ultra-short range nature of the transmitter, the identifier need not be associated with a particular patient such as in prior art inventions, instead, the identifier may be associated with the type of sensor unit. Thus there are a limited number of different identifiers required, the minimum number of identifiers being the number of different sensors located on a particular patient. The ultra-short range nature of the transmitter reduces the number of sensor units that could interfere with each other. Furthermore, by limiting the transmission power of the sensor units, the sensor units are less likely to interfere with other electronic medical devices and instrumentation.

The ultra-short range nature of the transmitter is accomplished by using a very low power transmission, such as less than approximately 1 mW or other attenuating means. The precise transmission power depends upon the distance in which the signal should attenuate, the type of antennas used in the system, as well as the type of modulation scheme used and the frequency used, and other factors such as are known in the field of communications. Preferably, the distance is less than approximately 12 feet, but the present invention also contemplates that this distance may be even shorter or in certain instances longer. In addition, preferably the power density is low, for example under approximately 150 $\mu W/cm^2$. The present invention contemplates that other higher power densities may also be used, but lower power densities better protect the patient from electromagnetic radiation exposure. The present invention contemplates that the broadcast signal may use any number of modulation schemes and may operate on a variety of frequencies. For example, the broadcast signal can be an FM signal operating at between 88 and 108 MHz such as may be used in FM radio and hearing aid devices, or could be GFSK operating in the 2.4–2.6 GHz band or any other type of modulation scheme or frequency such as is known in the art. Similarly, the signal can be broadcast as a spread spectrum signal at a frequency within the range of 902 MHz to 960 MHz. Other modulation schemes include, but are not limited to AM, QPSK, BPSK, FSK, and others. The present invention contemplates operation with any number of narrow band or wideband systems in any number of modes of operation and using any number of protocols that are capable of providing an ultra-short range link with low transmission power, low power density, or other attenuation capabilities as described or as otherwise known in the art.

Patient unit 10 has a receiving antenna 12 electrically connected to the sensor receiver 14. The sensor receiver 14 receives information from each sensor unit associated with a patient. The sensor receiver 14 is electrically connected to interleaver 16. Interleaver 16 may be implemented on a processor, microcontroller, microprocessor, digital signal processor, ASIC, or integrated circuit. Interleaver 16 receives information from the various sensor units associated with a patient and prepares the information for transmission. The present invention contemplates that the interleaver may take the patient data and place it in a single telemetry string for identification purposes, send separate strings associated with each sensor, or otherwise provide identifiers or other formatting and translation as a particular technology, environment, or other circumstances would suggest. The patient unit 10 may also have an optional biosensor 17. When the patient unit 10 includes the biosensor 17, the interleaver 16 receives information from biosensor 17 as well as the sensor receiver 14 and prepares this information for transmission.

Figure 2:
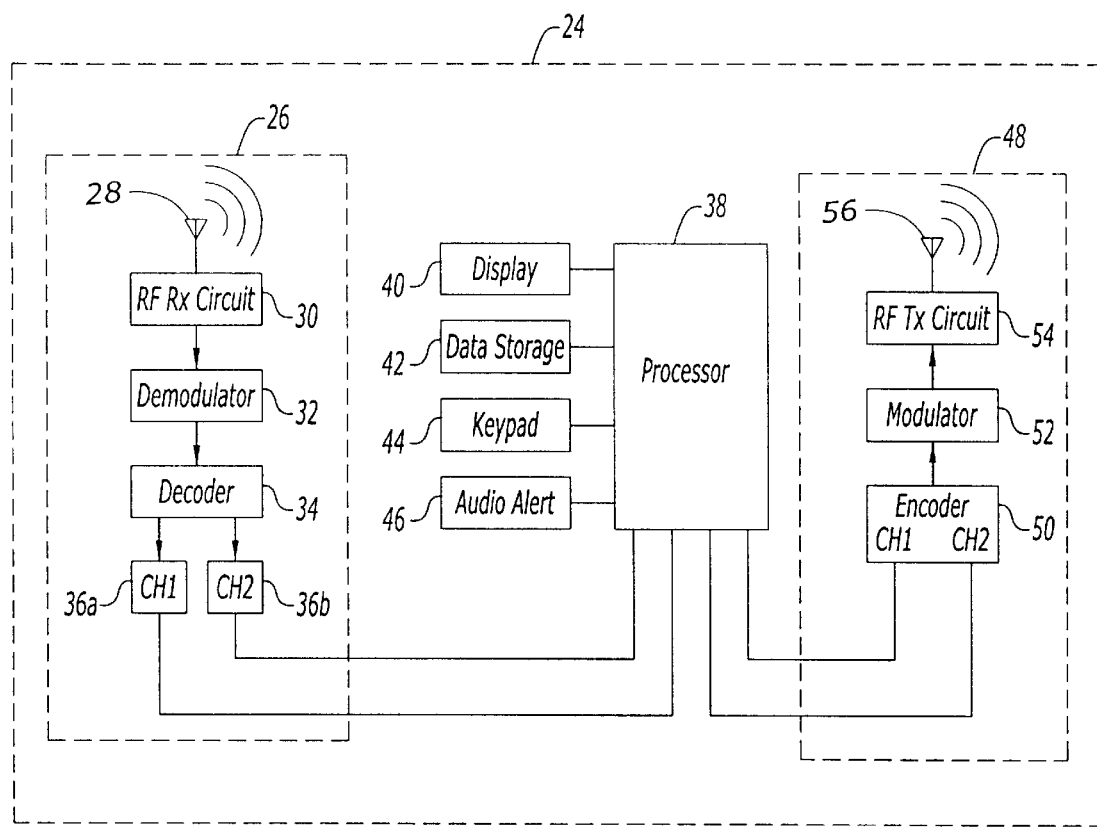
FIG. 2 is a schematic diagram of one embodiment of a medical monitor.

The patient transceiver 18 receives the data from interleaver 16 and transmits the information through antenna 20 to the multi-channel monitor unit 24. It is to be appreciated that patient transceiver 18 may be replaced by a transmitter, however, two way-communication provides additional flexibility. For example when a transceiver is used, the monitor unit 24 may request transmissions from the patient unit 10, or retransmissions if necessary. It is further to be appreciated that the patient transceiver may be a BLUETOOTH™ transceiver, an IEEE 802.11b compatible receiver or other receiver such as may be well known. The present invention is not limited to a particular type of wireless technology in this link. The multi-channel monitor unit 24 may receive information from multiple patient units through use of multiple channels. The multi-channel monitor unit 24 is best shown in FIG. 2. The monitor unit 24 has a receiver 26 for receiving the transmitted signal. The signal is received at antenna 28 which is electrically connected to an RF receiver circuit 30. The signal is demodulated at the demodulator 32 and then decoded at decoder 34 into multiple channels. Each channel is electrically connected to a processor 38. In place of a processor, a microcontroller, microprocessor, digital signal processor, ASIC, integrated circuit, or portion of an integrated circuit may also be used. The present invention contemplates that other types of receivers may be used for communication with the patient unit. For example, BLUETOOTH™ or IEEE 802.11 transceivers may be used to communicate the information. The present invention is not limited to a particular type of wireless technology in this link.

The processor 38 is electrically connected to a display 40. The display permits physiological information to be displayed. The display may be a LCD, plasma display, or other display that can provide a visual representations of information. Thus the patient or a medical personnel can observe the sensor readings. In addition, data storage unit 42 can be used. The data storage may be a magnetic media or a flash memory such as is well known and commercially available. For example, a Disk-on-Chip from M-Systems may be used to store the data A keypad 44 may also be connected to processor 38. The keypad permits optional entry of information into the processor 38. This permits the monitor unit 24 to be programmed. Thus, for example, different alert levels may be set, or other operations such as are well known. For example, if a certain physiological level meets or exceeds a certain level, an audio alert 46 can, be activated. The present invention contemplates this and other variations involving programmability of the monitor.

The processor 38 is also optionally connected to a transmitter 48. Receiver 26 and transmitter 48 may be a part of a single transceiver. When a transmitter 48 is used, multiple channels are electrically connected to an encoder 50. The encoder 50 is connected to a modulator 52 that modulates the signal, the modulated signal then entering the RF transmitter circuit 54. The signal is then transmitted through antenna 56.

The present invention contemplates that the monitoring unit may be a personal computer. The personal computer may include a monitor or display, a keyboard, a storage unit such as a hard drive and a wireless transceiver for communicating with the patient unit.

Figure 3:
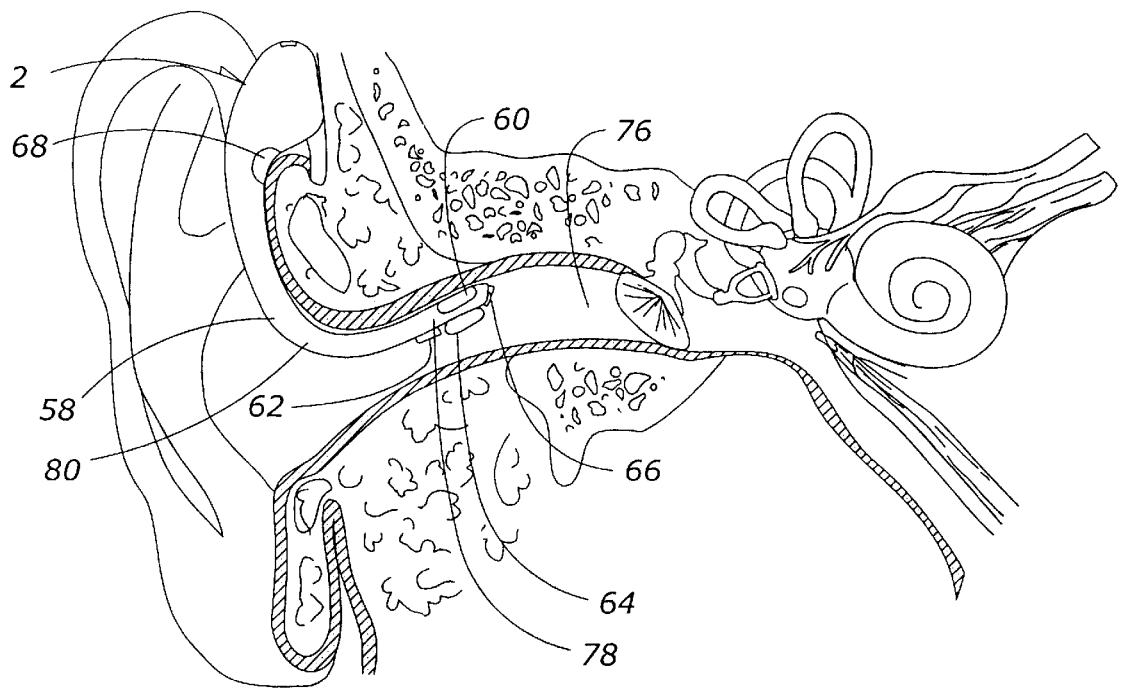
FIG. 3 is a diagram on one embodiment of medical sensors related to the ear.

FIG. 3 discloses an example of one sensor unit of the present invention. The sensor unit 2 is designed to be worn at the ear. An external canal portion 58 of the sensor unit 2 fits over the ear. The external auditory canal potion of the sensor unit includes a bone conduction sensor 58 and air conduction sensor 62 located on a resilient member 78. In addition, a body temperature sensor 64 is placed into the external canal near or at the medial segment of the sensor unit. The present invention further contemplates that the temperature sensor could also be placed at the luminal center of the external auditory canal. This placement of the body temperature sensor provides a highly accurate body temperature reading of core body temperature. This placement of the temperature sensor permits the core body temperature to be rapidly determined and to accurately reflect the gradients of the core body temperature. In addition, a pule oximeter 68 is placed against the skin of the temporal region anterior to the helix of the ear located near the incisura. This placement of the pulse oximeter provides excellent contact with the skin. In addition, this placement provides for added stability and for ease of measurement as the pulse oximeter is in close proximity with the temporal artery. A circuit portion 80 of the earpiece sensor unit provides additional circuitry and electronics, including a transmitter or transceiver. It is to be appreciated that where multiple sensors are a part of the same sensor unit, such as in the configuration shown in FIG. 3, only one transceiver or transmitter is required to transmit information received from the sensors.

Figure 4:
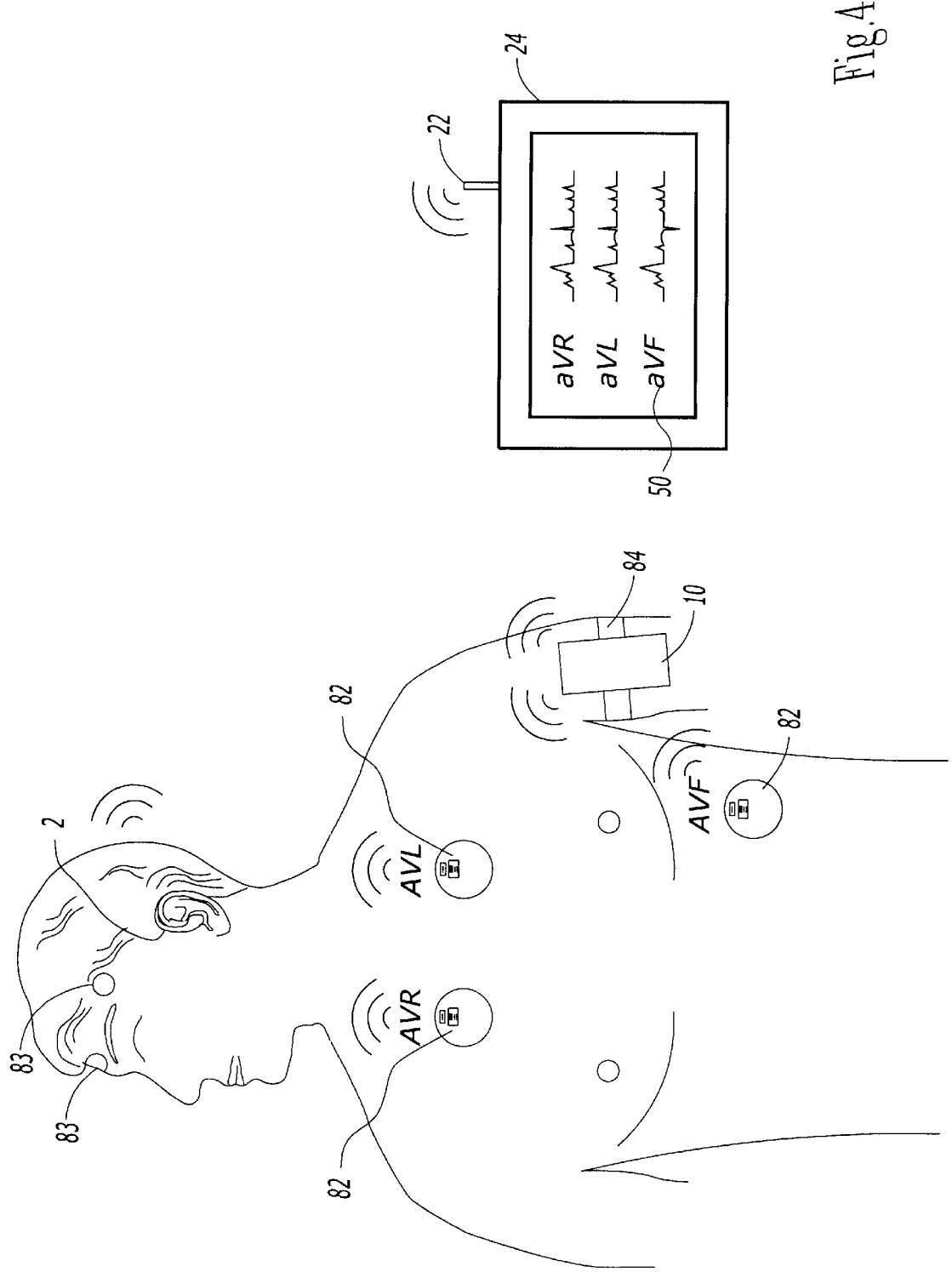
FIG. 4 is a schematic diagram which shows one embodiment of ECG electrodes and transmitters attached to a patient.

FIG. 4 shows the use of various biosensors. In FIG. 4, electrode sensor units 82 are attached to a patient. The ECG sensors or electrodes are placed in different locations such as $AV_R$, $AV_L$, and $AV_F$. Note that no wires connect the sensors to each other or to the patient unit 10. Earpiece 2 and its sensor unit may also be in wireless communication with patient unit 10.

Another example of a sensor unit that can be used is one that includes an electroencephalogram (EEG) sensor 83. One use of EEG electrodes is in determining the hypnotic state of patients so that anesthetic agents may be more effectively administered in a cost-effective and recovery-time minimizing manner. One example of an EEG sensor that can be used in this manner is the BISPECTRAL INDEX™ sensor available from Aspect Medical Systems. The present invention contemplates that EEG sensors, including EEG sensors used for the purpose of determining hypnotic state may be used in the present invention.

Patient unit 10 may be attached to a patient's armband 84 as shown. The patient unit 10 may also contain a sensor as previously described. When the patient unit is to be attached with an armband, the patient unit 10 can include a blood pressure sensor. The patient unit 10 may also be placed in a pocket, or attached to a belt, or other attachment that provides for convenient access to the patient unit or integrated into other monitor sensors, such as an EKG or EEG sensor. Patient unit 10 then may wirelessly communicate with monitoring unit 24.

Figure 5:
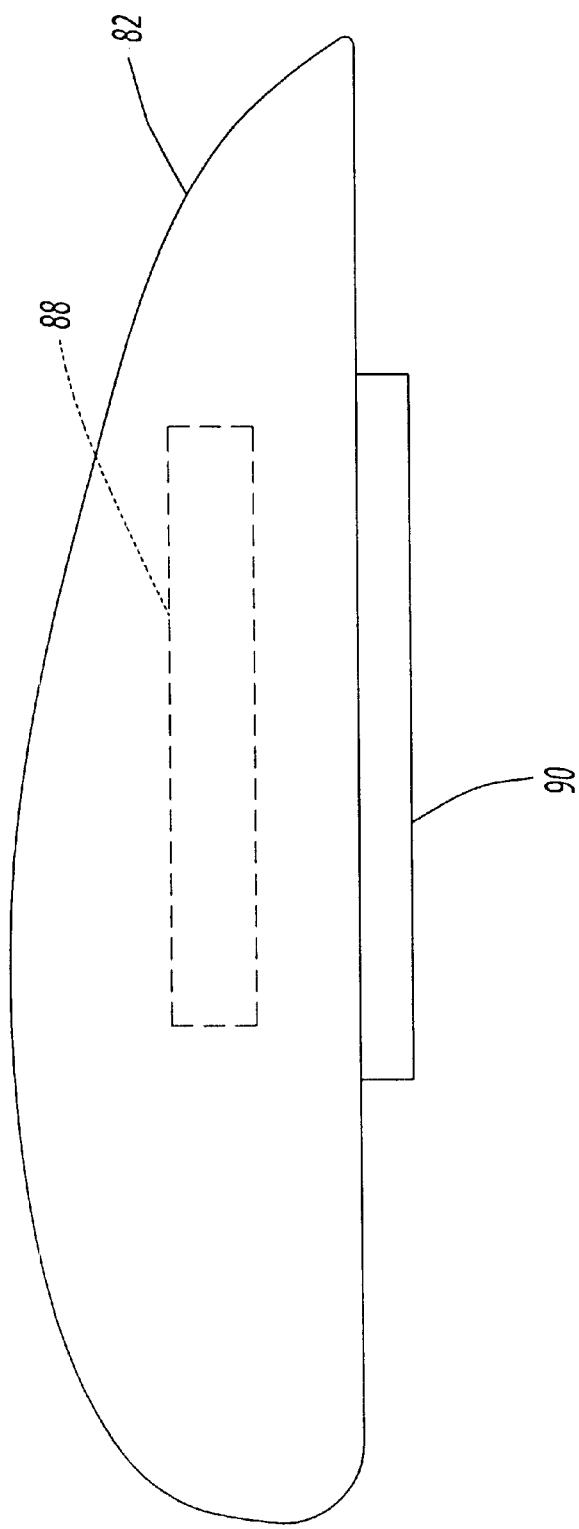
FIG. 5 is a side view of one embodiment of the ECG electrode and transmitter.

FIG. 5 is a side view of an electrode sensor unit 82. The sensor electronics 88, including the transmitter are housed within the electrode sensor unit 82. The sensor 90 is exposed so that it may be placed in contact with the patient's skin.

Figure 6:
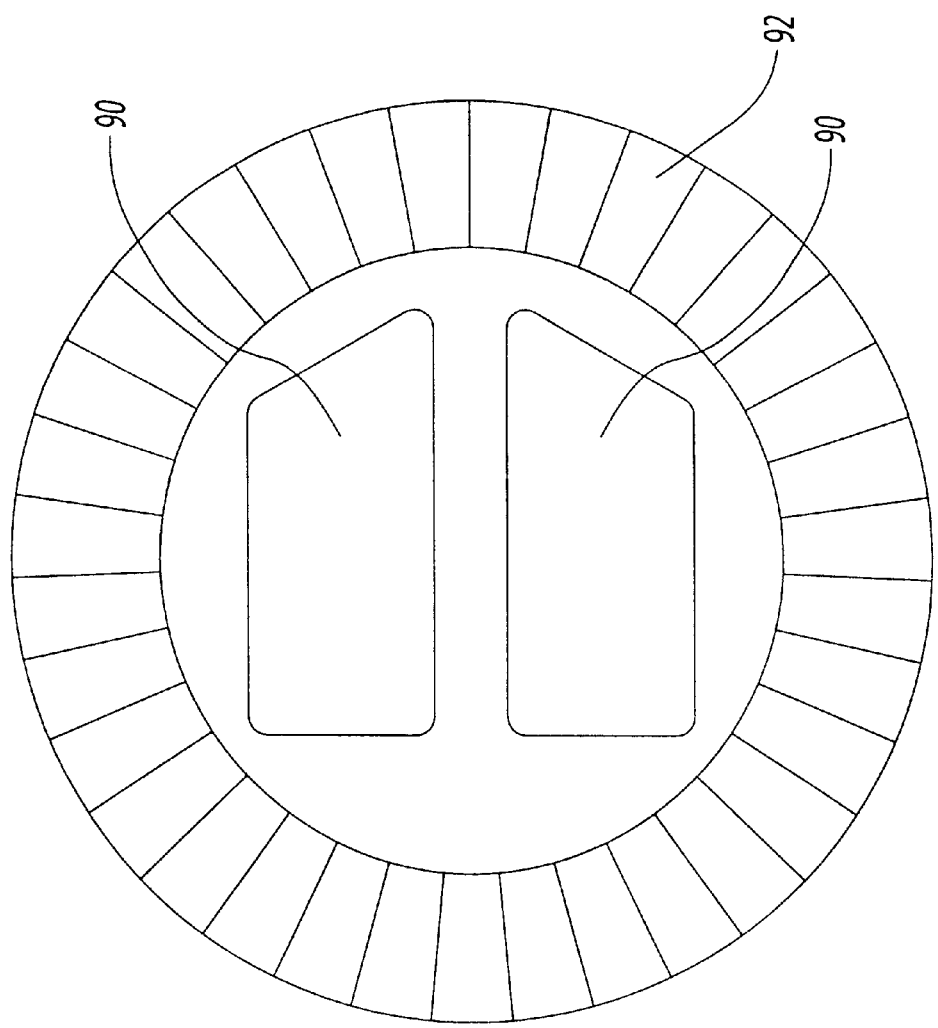
FIG. 6 is a bottom plan view of one embodiment of the ECG electrode and transmitter.

FIG. 6 shows a bottom view of the electrode sensor unit 82. Electrode sensor unit 82 includes a sensor 90. Sensor 90 may be a conventional ECG electrical sensor. Electrode sensor unit 82 also has an adhesive strip 92 attached to the bottom. The adhesive strip 92 is in a relationship to the sensor 90 such that sensor 90 rests flush against a patient's skin.

Figure 7:
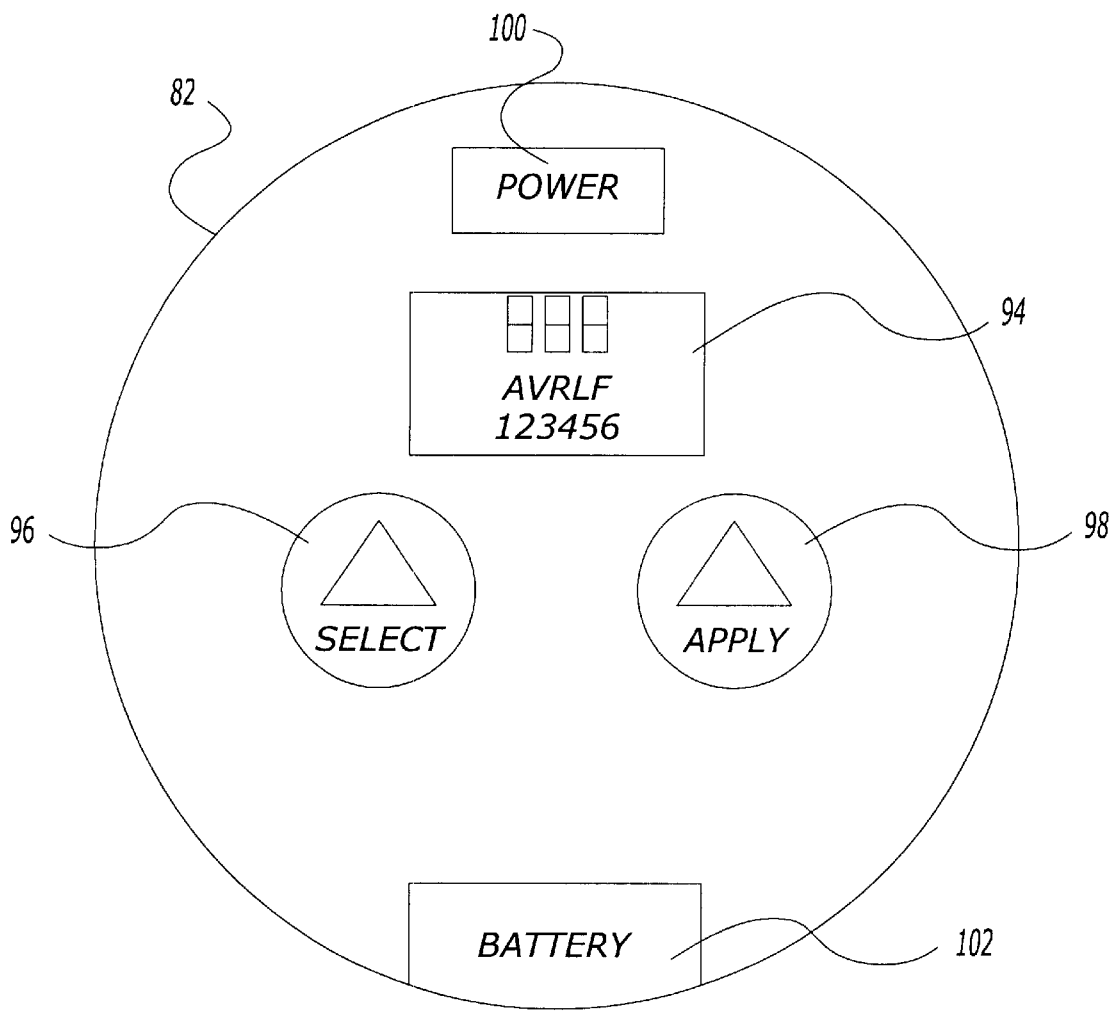
FIG. 7 is a top plan view of one embodiment of an ECG electrode and transmitter according to the present invention.

FIG. 7 shows a top plan view of the wireless electrode 82. Electrode sensor unit 82 includes a liquid crystal display (LCD) 94. LCD 94 displays information about the electrode, such as where the electrode should be placed (e.g., $AV_R$, $AV_L$). Electrode sensor unit 82 also includes a selection button 96 and an apply button 98. The selection button 96 is used to define the position of the sensor. The apply button 98 locks in the particular selection. Electrode sensor unit 82 is preferably battery powered. Electrode sensor unit 82 contains a battery hatch 102 for storing a battery. Note that rather than sensing a heart biopotential, other biopotentials could be sensed. For example, electromyograms, electroencephalograms, oxygen saturation, pulse rates, blood pressures, or body temperature could be sensed and transmitted to a remote receiver. The present invention is intended to cover these applications, as well as other situations not specifically mentioned herein.

Figure 8:
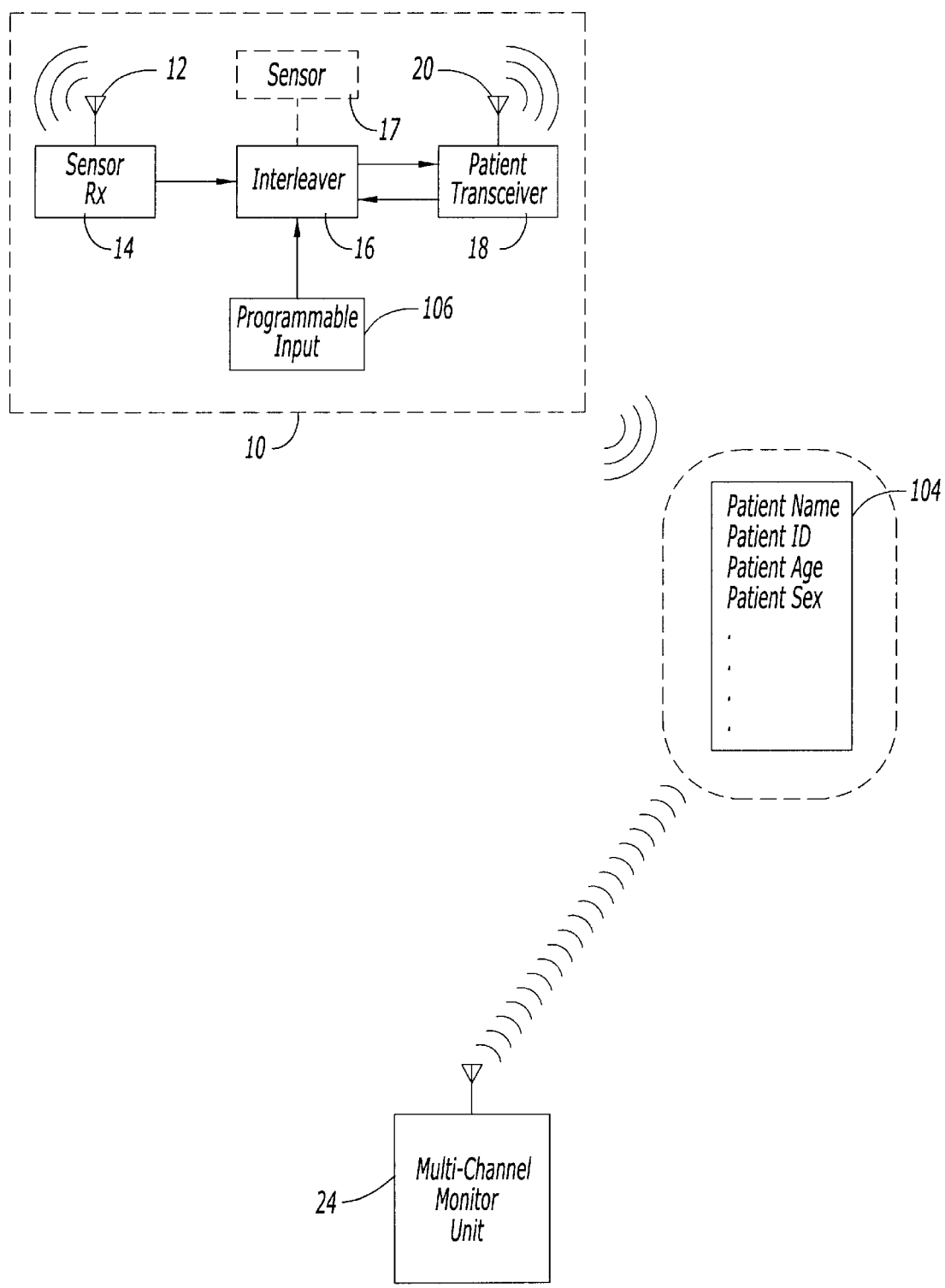
FIG. 8 is a block diagram of a patient monitor unit providing patient information to a monitor.

FIG. 8 shows additional options of the present invention. Additional information may be communicated between a patient unit 10 and a monitor unit 24. The information may include patient data including patient identifying information, medical information, and administrative information related to the patient. This information is stored in a memory of the interleaver 16. The memory may be a flash memory, an EEPROM, a magnetic memory, a solid state memory, an optical memory, or other memory such as may be known in the art. The size of the memory and type of memory used to store the patient information being selected based upon the amount of data to be stored, the speed of memory access required, and other considerations such as may be recognized by one skilled in the art. The patient information 104 stored in interleaver 16 may be requested by the monitor unit 24 or otherwise transmitted to the monitor unit 24. Monitor 24 can then display this information as well as the physiological information relating to the patient.

This patient information 104 may be entered into the patient unit 10 by sending the information from a monitor unit 24. It is to be understood that the monitor unit 24 may have a keypad or other input device and may be connected to a computer. In addition, the patient information 104 may be entered into the patient unit 10 through a programmable input 106 that is connected to the interleaver. The programmable input can be a keypad input, a serial input, a network input, or other input such as is well known in the art. This permits the patient unit 10 to be programmed with this information at bedside instead of at the location of the monitor. It is to be understood that the present invention is not limited to the particular type of input used or by the particular type of patient information used.

A general description of the present invention as well as preferred embodiment has been set forth about. Those skilled in the art will recognize and will be able to practice additional variations and the methods and devices described which fall within the teachings of this invention. Accordingly, all such modifications and additions are deemed to be within the scope of the invention which is to be limited only by the claims appended hereto.

I claim:

1. A biosensor unit for sensing and transmitting human physiological information comprising:
   an ear canal temperature sensor for sensing temperature in a human;
   a transmitter electrically connected to the ear canal temperature sensor for receiving temperature information from the ear canal temperature sensor and transmitting the information across a distance; and
   the transmitter adapted to place information on the broadcast signal which identifies a type of biosensor.

2. The biosensor unit of claim 1 wherein the transmitter in the sensor unit has a power output of less than approximately 1 mW.

3. The biosensor unit of claim 1 wherein the transmitter in the sensor unit transmits with a power density of less than approximately 150 $\mu$W/cm$^2$.

4. The biosensor unit of claim 1 wherein the distance is less than approximately 12 feet.

5. The biosensor unit of claim 1 further comprising an ear pulse oximeter, the transmitter electrically connected to the external auditory canal temperature sensor and the ear pulse oximeter.

6. A medical monitoring system, comprising:
   a plurality of sensor units, each sensor unit having a biosensor and a transmitter, the biosensor for sensing physiological data, the transmitter for transmitting the physiological data across a distance;
   at least one patient unit adapted to be located on or near a patient, the patient unit receiving the physiological data from the sensor units, interleaving the physiological data and transmitting the interleaved physiological data; and
   a monitor unit having a receiver to receive the interleaved physiological data transmitted from at least one patient, a display for displaying the physiological data, and adapted for receiving interleaved physiological data from at least one patient unit.

7. The medical monitoring system of claim 6 wherein the transmitter in the sensor unit has a power output of less than approximately 1 mW.

8. The medical monitoring system of claim 6 wherein the transmitter in the sensor unit transmits with a power density of less than approximately 150 $\mu$W/cm$^2$.

9. The medical monitoring system of claim 6 wherein the distance is less than approximately 12 feet.

10. The medical monitoring system of claim 6 wherein at least one biosensor is an ear temperature sensor.

11. The medical monitoring system of 6 wherein at least one biosensor is an ear pulse oximeter.

12. The medical monitoring system of claim 6 wherein at least one biosensor is an ECG electrode.

13. The medical monitoring system of claim 6 wherein the sensor unit transmitter is further adapted to place information on the broadcast signal which identifies the type of biosensor.

14. The medical monitoring system of claim 6 wherein the patient unit further includes at least one biosensor, the patient unit receiving the physiological data from the sensor units and at least one patient unit biosensor, interleaving the physiological data and transmitting the interleaved physiological data.

15. The medical monitoring system of claim 14 wherein the patient unit includes a blood pressure biosensor.

16. A method of physiological monitoring comprising:

sensing physiological conditions of a body through a plurality of sensors;

wirelessly transmitting the physiological information from each sensor;

receiving the physiological information from a plurality of sensors at a patient unit;

interleaving the received physiological information at the patient unit;

wirelessly transmitting the interleaved information by the patient unit; and receiving the interleaved information at a monitor unit.

17. The method of claim 16 wherein the step of wirelessly transmitting the physiological information from each sensor further includes limiting the power of the sensor transmitter used to wirelessly transmit to less than approximately 1 mW.

* * * * *